US00PP29415P2

(12) United States Plant Patent
Smit

(10) Patent No.: US PP29,415 P2
(45) Date of Patent: Jun. 19, 2018

(54) ***CRASSULA* PLANT NAMED 'EC-CRAS-01'**

(50) Latin Name: *Crassula mesembryanthemoides*
Varietal Denomination: EC-CRAS-01

(71) Applicant: Obed Jacob Smit, Sappemeer (NL)

(72) Inventor: Obed Jacob Smit, Sappemeer (NL)

(73) Assignee: Eden CollecTion B.V., Sappemeer (NL)

( * ) Notice: Subject to any disclaimer, the term of this patent is extended or adjusted under 35 U.S.C. 154(b) by 0 days. days.

(21) Appl. No.: 15/530,130

(22) Filed: Dec. 5, 2016

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new cultivar of *Crassula* plant named 'EC-CRAS-01' that is characterized by an upright and freely branching habit and light grey succulent leaves that are covered with dense hairs.

1 Drawing Sheet

Botanical classification: *Crassula mesembryanthemoides*.
Variety denomination: 'EC-CRAS-01'.

BACKGROUND OF THE INVENTION

The present invention relates to a new and distinct cultivar of *Crassula* plant botanically known as *Crassula mesembryanthemoides* and hereinafter referred to by the cultivar name 'EC-CRAS-01'.

'EC-CRAS-01' originated from the crossing of the female or seed parent, a proprietary *Crassula mesembryanthemoides* cultivar identified as hybrid 1 (not patented) and the male or pollen parent, a proprietary *Crassula mesembryanthemoides* cultivar identified as hybrid 2 (not patented). The crossing was conducted in 2012 in Sappemeer, Netherlands. The resulting seeds were subsequently planted and grown. The cultivar 'EC-CRAS-01' was selected by the inventor in 2013 in a controlled environment as a single plant within the progeny of the stated cross in a cultivated area of Sappemeer, Netherlands.

Asexual reproduction of the new cultivar 'EC-CRAS-01' first occurred by leaf cuttings in 2013 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Crassula* cultivar 'EC-CRAS-01'. These traits in combination distinguish 'EC-CRAS-01' as a new and distinct cultivar apart from other existing varieties of *Crassula* known by the inventor.

1. *Crassula* 'EC-CRAS-01' exhibits an upright habit.
2. *Crassula* 'EC-CRAS-01' exhibits a freely branching habit.
3. *Crassula* 'EC-CRAS-01' exhibits light grey succulent leaves that are covered with dense hairs.

*Crassula* 'EC-CRAS-01' can be compared to plants of the *Crassula tetragona* species and to plants of the *Crassula*

*congesta* species. 'EC-CRAS-01' is distinguishable from plants of the *Crassula tetragona* species by the following characteristics:

1. *Crassula* 'EC-CRAS-01' exhibits a freely branching habit. In comparison, plants of the *Crassula tetragona* species do not readily branch.
2. *Crassula* 'EC-CRAS-01' exhibits light grey succulent leaves that are covered with dense hairs. In comparison, plants of the *Crassula tetragona* species have light grey succulent leaves that do not have hairs.

'EC-CRAS-01' is distinguishable from plants of the *Crassula congesta* species by the following characteristics:

1. *Crassula* 'EC-CRAS-01' exhibits an upright habit. In comparison, plants of the *Crassula congesta* species have a spreading, bushy habit.
2. *Crassula* 'EC-CRAS-01' exhibits light grey succulent leaves that are covered with dense hairs. In comparison, plants of the *Crassula congesta* species have grey green succulent leaves with few hairs.

'EC-CRAS-01' is distinguishable from the female parent plant by the following characteristics:

1. *Crassula* 'EC-CRAS-01' exhibits light grey succulent leaves that are covered with dense hairs. In comparison, the female parent plant has leaves that are more green-grey in color.
2. *Crassula* 'EC-CRAS-01' exhibits an overall plant height that is larger than the overall plant height of the female parent plant.

'EC-CRAS-01' is distinguishable from the male parent plant by the following characteristics:

1. *Crassula* 'EC-CRAS-01' exhibits light grey succulent leaves that are covered with dense hairs. In comparison, the male parent plant has leaves that are more green-grey in color.
2. *Crassula* 'EC-CRAS-01' exhibits leaves that are longer than the leaves of the male parent plant.

BRIEF DESCRIPTION OF THE DRAWING

The accompanying photograph illustrates the distinguishing traits of *Crassula* 'EC-CRAS-01'. The photograph shows an overall view of a 20 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Crassula* cultivar named 'EC-CRAS-01'. Data was collected in Sappemeer, Netherlands from 20 week old plants grown in a glass greenhouse in 10.5 cm. diameter containers. The time of year was Winter and the temperature range was 18-22 degrees Centigrade during the day and 16-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-CRAS-01' has not been tested under all possible conditions and phenotypic differences may be observed with variations in environmental, climatic, and cultural conditions, however, without any variance in genotype.

Botanical classification: *Crassula mesembryanthemoides* 'EC-CRAS-01'.

Annual or perennial: Perennial.

Parentage: 'EC-CRAS-01' resulted from the crossing of the female or seed parent, a proprietary *Crassula mesembryanthemoides* cultivar identified as hybrid 1 and the male or pollen parent, a proprietary *Crassula mesembryanthemoides* cultivar identified as hybrid 2.

Plant type: Pot plant.

Plant shape: Flattened globose.

Growth habit: Broad upright.

Suitable container size: 7 cm. pots or larger.

Plant height: 10.3 cm.

Plant width: 21.7 cm.

Vigor: Low to moderate.

Growth rate: Low to moderate.

Low temperature tolerance: 5° Centigrade.

High temperature tolerance: 40° Centigrade.

Propagation: Leaf cuttings.

Time to initiate roots (summer): 7 days at 18 to 20° C.

Time to initiate roots (winter): 10 days at 18 to 20° C.

Time to produce a rooted cutting (summer): 28 days at 18 to 20° C.

Time to produce a rooted cutting (winter): 35 days at 18 to 20° C.

Crop time: Approximately 20 weeks in Sappemeer, Netherlands.

Root system: Dense and fine.

Plant fragrance: None.

Pinching: Not required, but improves branching when performed.

Stem:

*Branching habit.*—Main branches with lateral branches.

*Basal branching.*—Yes.

*Number of main branches per plant.*—Average 6.

*Number of lateral branches per plant.*—Average 9.

*Main branch dimensions.*—7.2 cm. in length and 0.6 cm. in width.

*Internode length.*—1.4 cm.

*Stem shape.*—Rounded.

*Stem appearance.*—Succulent.

*Stem luster.*—Slightly glossy.

*Stem pubescence.*—Densely covered with soft strigose hairs, 0.1 cm. in length, color 157D.

*Stem angle.*—Average 30 degrees from vertical.

*Stem strength.*—Moderately strong.

*Stem color* (*young*).—147C.

*Stem color* (*mature*).—145A to 145B.

*Internode color.*—145A to 145B.

Foliage:

*Leaf arrangement.*—Opposite.

*Compound or single.*—Single.

*Quantity of leaves per lateral branch.*—Average 12.

*Leaf shape.*—Narrow oblong, slightly curved sideways.

*Leaf aspect.*—Upper side flat, under side rounded.

*Leaf apex.*—Acute.

*Leaf base.*—Broad cuneate.

*Leaf dimensions.*—6.1 cm. in length and 1.2 cm. in width.

*Leaf thickness.*—0.9 cm.

*Texture* (*both surfaces*).—Succulent.

*Pubescence.*—Both surfaces densely covered with soft strigose hairs, 0.1 cm. in length, color 157D.

*Leaf luster.*—Moderately glossy both surfaces.

*Leaf rugosity.*—Non-rugose both surfaces.

*Leaf lobes.*—Not lobed.

*Leaf margin.*—Entire.

*Venation pattern.*—None visible.

*Young leaf color* (*upper surface*).—NN137A.

*Young leaf color* (*lower surface*).—NN137A, fading toward base 138B.

*Mature leaf color* (*upper surface*).—NN137A.

*Mature leaf color* (*lower surface*).—137B.

*Leaf attachment.*—Sessile.

Flower: 'EC-CRAS-01' has not produced flowers to date.

Fruit and seed: 'EC-CRAS-01' has not produced fruit or seed to date.

Disease and pest resistance: Disease and pest resistance has not been observed.

The invention claimed is:

1. A new and distinct variety of *Crassula* plant named 'EC-CRAS-01' as described and illustrated.

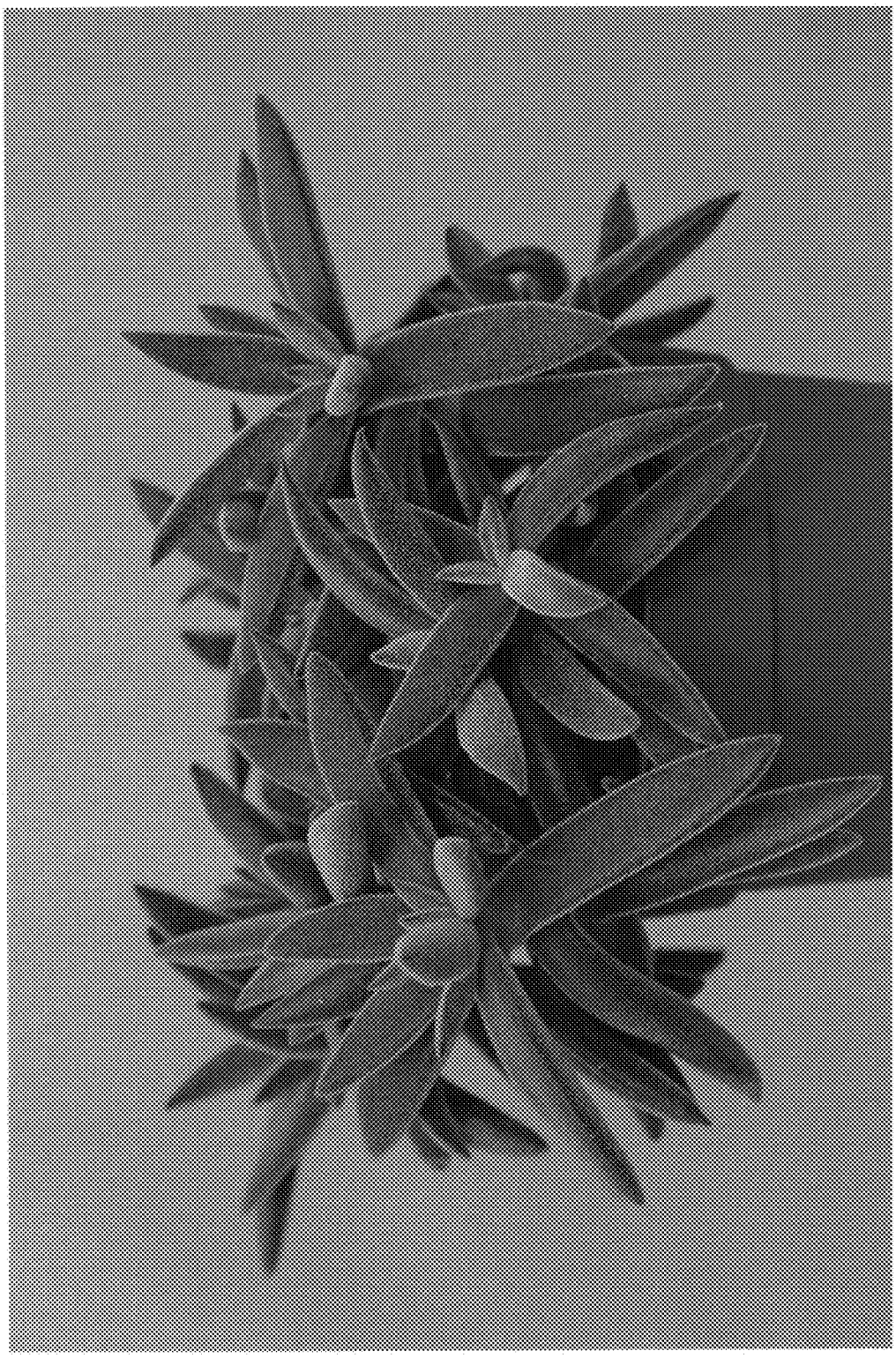

* * * * *